(12) United States Patent
Kaufman et al.

(10) Patent No.: US 7,260,863 B2
(45) Date of Patent: Aug. 28, 2007

(54) SURGICAL SCRUB BRUSH AND CLEANER APPARATUS

(75) Inventors: Jack W. Kaufman, Merrick, NY (US); James Brown, Armonk, NY (US)

(73) Assignee: Biomed Packaging Systems Inc., Norwalk, CT (US)

( * ) Notice: Subject to any disclaimer, the term of this patent is extended or adjusted under 35 U.S.C. 154(b) by 0 days.

(21) Appl. No.: 11/141,938

(22) Filed: Jun. 1, 2005

(65) Prior Publication Data

US 2006/0272114 A1 Dec. 7, 2006

(51) Int. Cl.
*A47L 13/12* (2006.01)
*A47L 13/16* (2006.01)

(52) U.S. Cl. .......................... 15/114; 15/160; 15/210.1; 15/220.4; 15/244.1; 15/244.4

(58) Field of Classification Search .................. 15/114, 15/160, 210.1, 220.4, 104.04, 244.1, 244.4
See application file for complete search history.

(56) References Cited

U.S. PATENT DOCUMENTS

| | | | | |
|---|---|---|---|---|
| 2,221,128 A | * | 11/1940 | Bates ........................ 15/244.1 |
| 2,865,036 A | * | 12/1958 | Poritz ........................ 15/119.2 |
| 3,002,213 A | * | 10/1961 | Lindstrom .................. 15/244.1 |
| 3,447,181 A | * | 6/1969 | Coker et al. ............. 15/104.94 |
| 4,181,446 A | * | 1/1980 | Kaufman ....................... 401/9 |
| 4,517,702 A | * | 5/1985 | Jackson ........................ 15/114 |
| 4,716,615 A | * | 1/1988 | Whitehead et al. ........ 15/220.4 |
| 4,903,365 A | * | 2/1990 | Kaufman ..................... 15/110 |
| 5,231,728 A | * | 8/1993 | Schillinger ................. 15/220.4 |
| 5,312,197 A | * | 5/1994 | Abramson ..................... 401/6 |
| 5,351,356 A | * | 10/1994 | Townsend, Jr. ............... 15/114 |
| 5,640,737 A | * | 6/1997 | Boggs ........................ 15/118 |
| 6,289,547 B1 | * | 9/2001 | Narula et al. ............... 15/167.3 |
| 6,485,822 B1 | * | 11/2002 | Osiecki et al. ........... 428/316.6 |
| 2001/0029967 A1 | * | 10/2001 | McDonough .................. 134/6 |
| 2003/0156884 A1 | * | 8/2003 | Teh ............................. 401/39 |

* cited by examiner

*Primary Examiner*—Mark Spisich
(74) *Attorney, Agent, or Firm*—Lackenbach Siegel, LLP

(57) ABSTRACT

A scrub brush-sponge includes a base provided with a recessed peripheral lip, which has a plurality of attenuated regions configured to minimize the resistance of the base to external bending forces, and a sponge coupled to the base and made from polymeric material, which may have as low a PPI as 10. The sponge is configured so that it can effectively surround at least a substantial peripheral portion of instruments or portions to be treated with fluid, which is contained within the sponge, without applying substantial external forces to the base.

12 Claims, 2 Drawing Sheets

SURGICAL SCRUB BRUSH AND CLEANER APPARATUS

BACKGROUND OF THE INVENTION

1. Field of the Invention

The present invention relates to scrub sponges, and particularly, relates to scrub brush-sponges associated with a variety of medical procedures and adaptable for treating medical instruments.

2. Description of the Related Art

Numerous brush structures are known in the art. Some of these structures are functionally effective as well as convenient in use or ergonomic. While a minor amount of brush modification continues, surprisingly, scrub brushes used by medical professionals have not been substantially modified for quite some time. Structurally, a typical scrub brush has a base coupled to a rectangular sponge, which is saturated with antiseptic, germicide and/or soapy fluid and has a generally rectangular cross-sectional shape.

In the medical field, many scrub brush-sponges have a great variety of adaptations. Besides traditional functions, such as cleaning the hands of the professional, removing blood and treating wounds, the brushes also may be used for cleaning a variety of medical instruments, particularly those instruments that need to be sterilized or, at least, cleaned repeatedly during a surgical procedure.

While such rectangular sponges may effectively clean flat surfaces, they may be less effective while treating annular surfaces, which are rather typical for a great variety of medical instruments. Particularly, many of the medical instruments, which are used for invasive procedures such as colonoscopy or other diagnostic procedures, to name a few, have substantially circular bodies. Customarily, surgical medical instruments undergo thorough sterilization before the beginning of the medical procedure. However, as mentioned above, many instruments can be reused during the same medical procedure and, thus, have to be repeatedly cleaned before each subsequent use.

Since the base of the typical brush may not be sufficiently flexible, the user has to apply excessive bending forces to flex the base so that the sponge would surround the annular body of the medical instrument. Otherwise, without flexing the base, a typical rectangular sponge may clean only a segment of the entire annular body, which leads to a time-ineffective cleaning process in a situation often requiring the instantaneous availability of any given instrument.

Assuming that the user does not experience any difficulty in flexing the scrub brush-sponge for cleaning medical instruments, the scrub still may remain inefficient, because the surface of the sponge is typically smooth. The smoothness, at least partially, depends on the number of pores per inch (PPI). The higher the PPI the smoother the surface. And while a typical smooth surface is perhaps pleasant for cleaning the user's hands, it may be ineffective for cleaning the metallic or other surfaces of medical instruments.

A need, therefore, exists for a scrub brush-sponge configured with an ergonomic structure that enables the user to clean medical instruments in a time-effective manner Still a further need exists for a scrub brush-sponge having a structure that can be sufficiently flexible to enable the user to effectively clean medical instruments in a relatively effortless maimer.

Another need exists for a scrub brush-sponge configured with a sponge that is characterized by as relatively low PPI for effectively scrubbing the surface of numerous medical instruments.

SUMMARY OF THE INVENTION

The present invention is directed to a scrub brush-sponge that satisfies at least one of these needs. The inventive brush includes a base made from flexible material and a sponge coupled to the body and saturated with a selected fluid. When during an invasive procedure, the professional performing the procedure needs to reuse a previously used medical instrument, he or she may sterilize or clean this instrument with the inventive brush. Since many of the medical instruments have a substantially annular shape, the sponge of the inventive scrub is provided with a channel, which is shaped so that when the professional places the instrument within the channel, the inner surface of the sponge surrounds at least a portion of instrument's body.

Upon applying an insignificant or minor amount of manipulative force to the base of the inventive brush-sponge, the professional is then able to bring opposing sidewalls of the sponge towards one another and, depending on the outer dimensions of the instrument, practically surround the entire periphery of the instrument's body by the sponge. Finally, displacing the brush-sponge and instrument relative to one another, the professional can treat the surface of the instrument in a time-effective and efficient manner.

As is known, the sponge may be used for numerous purposes including, for example, cleaning the hands of the professional, treating cuts and wounds and, as discussed above, sterilizing instruments. Depending on the particular application, the surface of the sponge may be relatively smooth, which is particularly important while treating the patient's open wounds, or relatively rough, which may be advantageous for cleaning the instruments.

Accordingly, one criterion as the number of pores per inch (PPI) plays a particularly important role for choosing the sponge for a particular purpose. Increasing the PPI leads to a relatively smoother surface, while decreasing the PPI makes the surface of the sponge relatively more abrasive. In accordance with one of the inventive aspects, the PPI can be as low (at the extreme) as about 10 and as high as about 200 pores per inch. Setting the PPI is a selective compromise depending upon a variety of factors proposed in this invention.

In addition to the smoothness of the surface, a relatively high PPI improves the capacity of the sponges to distribute treating fluid numerous times (meaning the high PPI sponge retains a lot of fluid and produces suds easily), but a high PPI also reduces the volume of the delivered fluid. In contrast, sponges with a relatively low PPI, for example a PPI from 10 to 60, delivers a greater volume of liquid-fluid at once, but thereafter becomes dry rather quickly. In other words, the low PPI sponge suds easily but also releases a higher volume of washing/cleaning/sterilizing fluid to carry away released debris.

As mentioned above, the professional, of course, has to apply some amount of manipulative force to the base of the inventive brush in order to surround (bend) a portion of the brush or sponge about a portion of the instrument's body as the dimensions of the sponge's channel or brush channel would allow.

To facilitate bending of the base in either direction (for scrubbing or sponge usage), which causes the sidewalls of the base to approach one another in either direction, the base of the inventive scrub brush-sponge has a plurality of attenuated hinge regions provided along the edges of the base so as to minimize bending and twisting resistance to the applied force. Alternatively or, preferably, in combination with the hinge regions, the edges or corner of the base are recessed to even further increase the flexibility of the base. In an additional embodiment, both the edges of the base and the base floor itself may be provided with cut-lines, or cut out portions, that act as slip plains and allow sections of the base edge to move relative to one another or that allow a floor of the base to shift relative to an adjacent the base edge portion.

The outer side of the base has a plurality of bristles arranged in numerous rows. Bristles defining a group of rows, which are located substantially midway between opposite edges of the base, have a height gradually decreasing towards the centerline of the base so that the free ends of the non-uniform bristles define a C-shaped or U-shaped trough. Obviously, the width of the trough may be selected so as to receive a segment of the annular body of the instrument to be scrubbed. Of course, such adaptation of the inventive scrub brush-sponge does not exclude other, more traditional functions of the brush including, for example, cleaning nails.

These and other features and aspects of the present invention will become apparent from the following description read in conduction with the accompanying drawings.

DETAILED DESCRIPTION OF THE PREFERRED EMBODIMENTS

Figure 1:
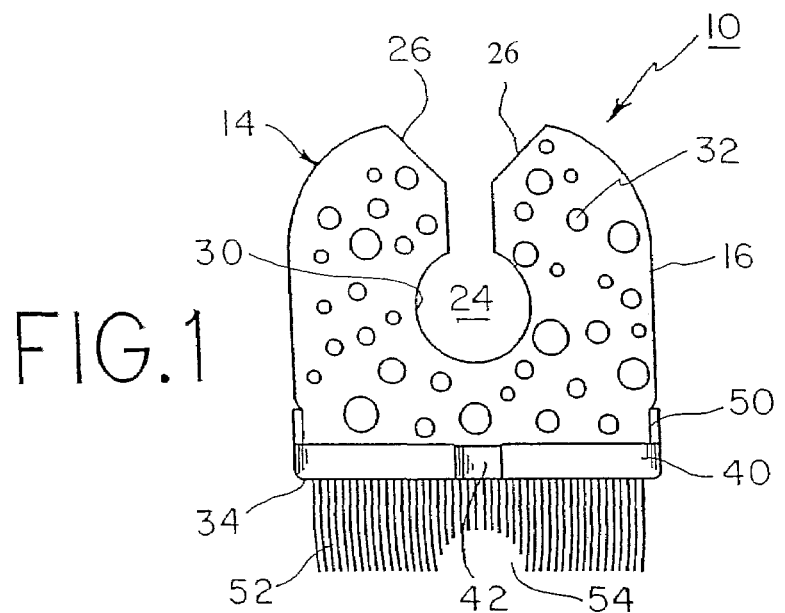
FIG. 1 is an elevational side view of one embodiment of the inventive scrub brush-sponge provided with a channel formed within a sponge member.

Reference will now be made in detail to several embodiments of the invention that are illustrated in the accompanying drawings. Wherever possible, same or similar reference numerals are used in the drawings and the description to refer to the same or like parts or steps. The drawings are in simplified form and are not to precise scale. For purposes of convenience and clarity only, directional terms, such as top, bottom, up, down, over, above, and below may be used with respect to the drawings. These and similar directional terms should not be construed to limit the scope of the invention in any manner. The words "connect," "couple," and similar terms with their inflectional morphemes do not necessarily denote direct and immediate connections, but also include connections through mediate elements or devices.

Figure 3:
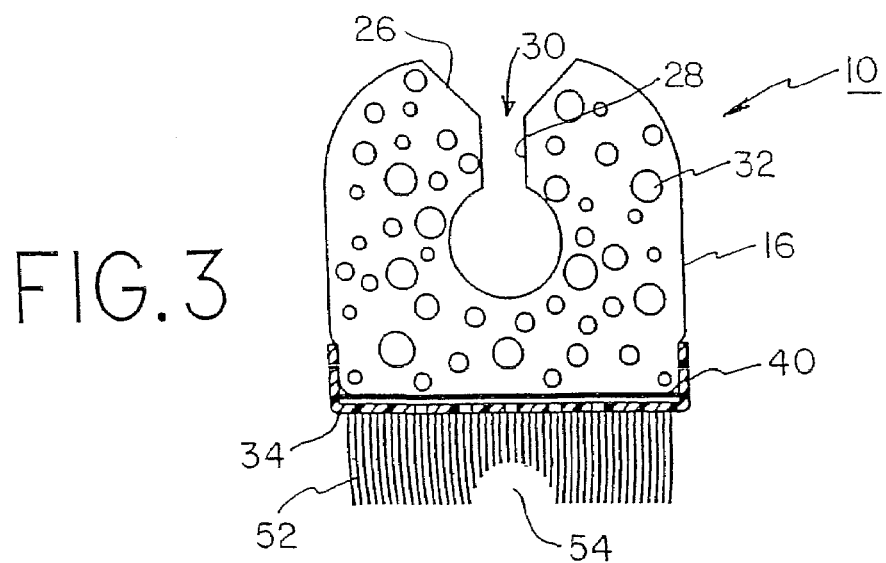
FIG. 3 is a cross-sectional side view of the inventive scrub brush-sponge of FIG. 1.
Figure 4:
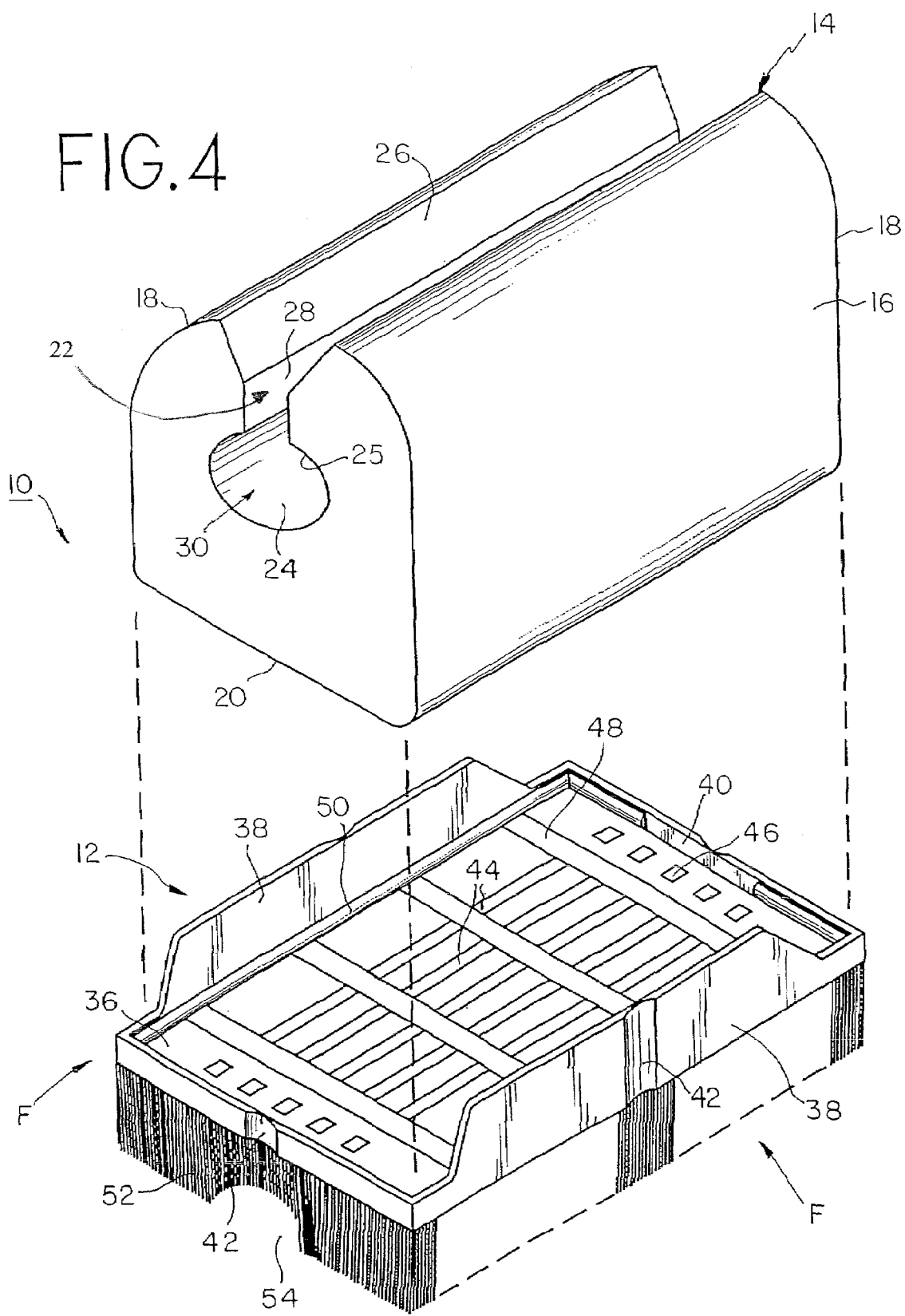
FIG. 4 is an exploded view of the inventive scrub brush-sponge configured in accordance with the embodiment shown in FIGS. 1 and 3.

FIGS. 1, 3 and 4 illustrate a scrub brush-sponge 10, which is configured to provide a treatment of an annular body of a medical instrument that can be used more than once during the same medical procedure including, but not limited to, colonoscopy. As shown in FIG. 4, scrub brush-sponge 10 includes a base 12 and a sponge 14 typically bonded to base 12. Coupling between the base and sponge may be realized in a variety of ways subject only to reliable contact between these components during the use of scrub brush-sponge 10. As a rule, a scrub brush-sponge is a disposable item and, in addition to cleaning of instruments, can perform standard operations such as cleaning the hands and nails of the professional, wetting and disinfecting the wounds of the patients and others.

As every other medical item, scrub brush-sponge 10 has to effectively operate for the intended purposes and be ergonomic so as to provide the professional with maximum possible convenience. Both criteria are readily met by the inventive brush-sponge due to a few inventive features that can be implemented separately or, preferably, in combination with one another.

To enhance cleaning of the instrument's body that may have an annular or polygonal cross-section, it is necessary that the opposing surfaces of sponge 14 and the instrument have as large a contact area as possible. Substantially surrounding the instrument by sponge 14 allows the professional to sterilize the instrument's surface in a time-effective manner as well as to have a reliable grip by pressing the sponge against the instrument. Providing sponge 14 with a channel 30 (FIGS. 1, 3 and 4), which is configured to receive the instrument's body, attains this objective.

In use, the professional places the instrument within channel 30 by spreading sidewalls 18 of sponge's body 16 (FIG. 4) apart and eventually lands the instrument within an arcuate region 24 of channel 30. Arcuate region 24 may be variously dimensioned to accommodate differently sized and shaped instruments, but, ideally, this region is large enough to have an inner surface 25 (FIG. 4) of sponge 14 extend complementary to a substantial peripheral segment of the instrument.

Thereafter, the professional applies an insignificant compression force F (FIG. 4) to the opposite sides of base 12 so as to bring free ends of sidewalls 18 of sponge 14 closer to one another. As a consequence, a gap between outer free end regions of sidewalls 18 above the inserted instrument is minimized and may be closed, which allows inner surface 25 of sponge 12 to substantially surround the instrument. Displacement of scrub brush-sponge 10 and the instrument to be sterilized relative to one another completes the treatment of the instrument in a time effective and efficient manner. Obviously, this positioning process may be reversed, and the instrument may be placed within trough 54 and the base curved to increase scrubbing contact.

Free end regions of sidewalls 18 each have a respective rectilinear region 22 (FIG. 4) of channel 30, which is configured with a pair of inner sub-region 28 and outer sub-region 26 (FIGS. 1, 3 and 4). While inner sub-regions 28 of opposing rectilinear regions 22 lie in substantially parallel planes, outer sub-regions 26 diverge outwards from one another when the professional does not apply compression force F to base 12. If the instrument to be sterilized has dimensions comparable to or larger than the dimensions of arcuate or annular region 24 of channel 30, the professional may apply an additional compression force sufficient to bring inner end sub regions 28 together and completely surround the instrument within channel 30. Preferably, outer sub regions 26 do not abut one another in response to applying compression force F and, as a result, form a V-shaped path guiding squeezed fluid away from the hands of the professional rather than allowing it to flow over the hands.

The sponge 14 is made from polymeric material, such as polyurethane foam and, as mentioned before, can be adapted for various medical procedures in addition to cleaning medical instruments. Depending on the PPI, the sponge can be successfully adapted, among others, in orthopedic operations, procedures performed by podiatrists and oculists. Clearly, each of these medical procedures requires that sponge 14 have a relatively smooth or rough outer surface. For example, obese people preferably use a smooth sponge for cleaning and disinfecting body parts that are covered by folds of fat. To provide such a smooth surface, sponge 14 may have its body 16 (FIG. 4) formed with a higher concentration of pores 32 (FIG. 1), whose PPI may vary from about 70 to about 200, resulting in a smoother surface texture and greater SVD forming capacity.

In contrast, cleaning the instruments may be more efficient if sponge 14 would have a relatively abrasive outer surface. For this purposes, body 16 of sponge 14 may have a very low PPI ranging between about 10 and about 15. It should be obvious to those skilled in the art that decreasing pore count increases relative pore volume.

Sponge 14 has a rather flat bottom 20 (FIG. 4), which is coupled to an inner side 36 (FIG. 4) of the bottom of base 12. To position sponge 14 in a desirable, centered position on base 12, the latter has a body made from of relatively firm but flexible polymeric material, such as polyethylene, and a peripheral lip which defines the bottom of base 12 and extends therefrom to peripherally abut the bottom portion of sponge 14. The lip includes two relatively long lip segments 38 bridged by relatively short lip segments 40 (FIG. 4). Since compression force F is typically, but not always, applied to long sides of base 12, long lip segments 38 have a greater height than short lip segments 40 and, therefore, engage a greater area of the bottom portion of sponge 14 to ensure that the latter does not voluntarily move out of engagement with base 12. The inner surface of lip segments 38,40 has a ledge 50 (FIG. 1 and 4) extending inwards from these segments and configured to press against the opposing surface of sponge 14, as better illustrated in FIG. 1. An adhesive joins sponge 14 with base 12, as shown.

Figure 2:
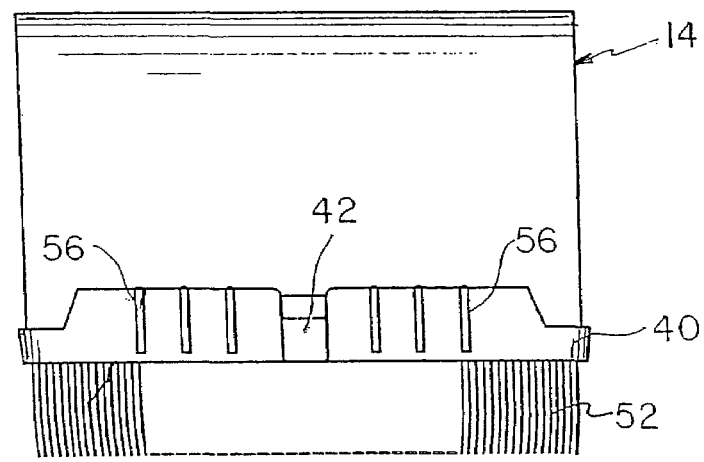
FIG. 2 is an elevational side view of another embodiment of inventive scrub brush-sponge and illustrates a recessed peripheral lip formed on the scrub's base.

Bending base 12 may not be an easy task without the improvements provided by the present invention. During use, the flexibility of base 12 is critical to proper functioning of sponge 14. To help the professional easily bend base 12, at least some of, but preferably all four, lip segments 38, 40 have attenuated hinge regions 42 (FIGS. 1, 2 and 4). When the professional applies compression force F, hinge regions 42 easily collapse providing minimal (substantially reduced) resistance to the applied force. Not only the area occupied by each hinge region is thinner than the rest of a respective lip, but also this area is arcuately indented either outwards or inwards, as illustrated in FIG. 4. Due to the convexity or concavity of the hinge regions, brush-sponge 10 can be repeatedly squeezed without damaging regions 42.

To further improve the flexibility of base 12, lip segments 38, 40 can also have a plurality of cut lines 56 (FIG. 2) defining, thus, a plurality of lip sub segments that can move relative to each other along cut-line slip plains. Cut lines 56 may terminate before reaching the bottom of the lip segments, as illustrated in FIG. 2. Alternatively, cut lines 56 may extend into the bottom of base 12 to aid increased torsional and arcuate curvature during use to aid scrubbing and sterilization.

To prevent accumulation of fluid squeezed out of sponge 14 and to further improve flexibility of base 12, its bottom is provided with an arrangement of elongated slots and holes 44, 46, respectively, (FIG. 4). The entire base can be molded in one piece with the aid of mold-cavity inserts for a first-shot and a second-shot injection as is well known per se. To reinforce base 12, its bottom may have additional reinforcing frame 48 (FIG. 4) including multiple spaced strips, which extend between relatively long lip segments 38 of the base.

An outer side 34 (FIGS. 1 and 3) of the base's bottom is molded with a plurality of rows of bristles 52 preferably made of the same material as base 12. Primarily, the bristles are used for cleaning the fingernails of the professional. In addition, the bristles may be used as a scrubbing surface for cleaning the instruments. Similarly to channel 30 formed in sponge 14, bristles 52 may be arranged so as to define a central trough 54 (FIGS. 1, 3 and 4) configured to receive a substantial portion the peripheral surface of the instrument. To form trough 54, bristles 52 arranged in central rows have their height gradually reducing towards the centerline of outer surface 34, whereas rows of bristles 52 located along opposite sides of outer surface 34 have uniformly dimensioned bristles. Accordingly, trough 54 may have a generally C-shaped or U-shaped cross-section.

Bristles 52 may be formed with uniform stiffness. Alternatively, the bristles forming outer rows may be made from relatively soft materials, making them ideal for the cleaning of fingernails or promoting the foaming of fluid, such as soap solution, which is contained in sponge 14. At the same time, the flexibility of bristles defining central rows may be lower so as to enhance the scrubbing effect.

In a first alternative example, while the sponge illustrated in FIGS. 1, 3 and 4 has a generally C-shaped or U-shaped cross-section, it may easily have a generally rectilinear or rectangular shape, as shown in FIG. 2. Furthermore, while the enhanced flexibility of the inventive scrub brush-sponge has been mainly explained as a result of applying compression forces for scrubbing surgical instruments, this flexibility can be equally useful in treating body portions that are difficult to access to difficult to clean. For instance, feet in general, and toes in particular, fingers, and the face are difficult to clean, particularly in the morbidly obese or in the violently injured to remove debris. In this regard, any bending or twisting force, not only the compression force, can be applied to the base so as to have the inventive scrub brush-sponge assume the desirable shape and clean properly.

In an alternative embodiment, the present invention may also be packaged as a surgical kit, combining the brush/sponge unit itself, but also a selected component in a sealed package. The sealed kit providing a ready-to-use cleansing and sterilization assembly. In one aspect of this type of alternative embodiment, the kit may include an antibiotic or fungicidal foaming fluid for surgical use or cleansing of surgical instruments. In another aspect of this alternative embodiment, the kit may include a grease cutting fluid for cleansing delicate mechanical parts in an industrial process. The benefits of providing a sealed ready-to-use kit are many. For example, a surgeon or other professional may tear open a sterilized ready-to-use scrub brush kit pre-loaded with cleansing fluid to clean and sterilize a surgical tool. In another example, a manufacturer may employ a pre-loaded brush kit to remove cutting oil from a complex mechanical shape.

In sum, although only a single or few exemplary embodiments of this invention have been described in detail above, those skilled in the art will readily appreciate that many modifications are possible in the exemplary embodiment(s) without materially departing from the novel teachings and advantages of this invention. Accordingly, all such modifications are intended to be included within the spirit and scope of this invention as defined in the following claims.

What is claimed is:

1. A scrub brush-sponge for treating a medical instrument, comprising:
   a base:

a sponge coupled to the base and provided with an inner surface, the inner surface defining a channel open away from the base and configured to receive a body of the medical instrument so that the inner surface of the sponge extends complementary to and is juxtaposed with a peripheral portion of the body of the medical instrument;

the channel has an inner substantially annular region and two outer substantially rectilinear regions opposing one another so that when no external force is applied to the sponge, the opposing rectilinear regions are spaced apart, and when the external force is applied to the sponge, the opposing rectilinear regions are displaceable towards one another so as to increase a contact area between the body of the medical instrument and the inner surface of the sponge;

the two opposing rectilinear regions of the inner surface of the sponge each have a respective pair of inner and outer sub-regions configured so that when the external compression force is not applied, the inner and outer sub-regions of each pair extend away from one another; and the inner sub-regions of the two opposing rectilinear regions of the inner surface of the sponge extend in substantially parallel planes, whereas the outer sub-regions extend in planes diverging outwardly from one another.

2. The scrub brush-sponge of claim 1, wherein:

the sponge has a bottom bonded to the base and two spaced apart side walls bridged by the bottom and extending outwardly therefrom so that, when no external force is applied to the base, the sponge has a substantially U-shaped or C-shaped cross-section, and when the external force is applied, the sponge tends to assume a substantially annular shape and to enclose the body of the medical instrument.

3. The scrub brush-sponge of claim 1, wherein:

the base has a respective bottom receiving the sponge and provided with at least one peripheral lip region, the at least one peripheral lip region extending upwards from the support surface and centering the sponge on the base.

4. The scrub brush-sponge of claim 3, wherein:

the peripheral lip has a plurality of hinge regions spaced from one another and each configured to increase flexibility of the base upon applying an external force to the base.

5. The scrub brush-sponge of claim 4, wherein:

the plurality of hinge regions each are at least one of a concavely or convexly configured shape for facilitating thereby flexing of the base in response to applying the external force.

6. The scrub brush-sponge of claim 4, wherein:

the plurality of hinge regions each have a respective thickness smaller than a thickness of adjacent portions of the peripheral lip.

7. The scrub brush-sponge of claim 3, wherein:

the peripheral lip has a plurality of cut lines shaped and dimensioned to increase flexibility of the base upon applying an external force.

8. The scrub brush-sponge of claim 7, wherein:

the plurality of cut lines each extend into the bottom of the base.

9. The scrub brush-sponge of claim 3, wherein:

the bottom of the base has a plurality of elongated slots opening into opposite inner and outer sides of the bottom, the slots being shaped and dimensioned to increase flexibility of the base upon applying an external force to the base.

10. The scrub brush-sponge of claim 9, wherein:

the outer side of the bottom of the base has a plurality of bristles inserted in rows of different height so that the outer side of the bottom of the base has a generally C-shaped or U-shaped trough spaced substantially uniformly from opposite edges of the bottom and dimensioned to receive an item for scrubbing.

11. The scrub brush-sponge of claim 3, wherein:

the peripheral lip of the base is endless and has an inner surface coextending with and pressing upon a bottom of the sponge so as to retain the sponge centered on the base as the base is being flexed upon applying and releasing an external force to the base.

12. The scrub brush-sponge of claim 1, wherein:

the sponge is made of foam having a PPI ranging between about 10 to about 200.

* * * * *